United States Patent [19]

Sanemitsu et al.

[11] 4,451,283
[45] May 29, 1984

[54] 5-OXO-2,5-DIHYDRO-1,2,4-TRIAZINES

[75] Inventors: Yuzuru Sanemitsu, Ashiya; Masao Shiroshita, Takarazuka; Shunichi Hashimoto, Toyonaka; Haruhiko Katoh, Nishinomiya; Hiroshi Matsumoto, Toyonaka, all of Japan

[73] Assignee: Sumitomo Chemical Company, Limited, Osaka, Japan

[21] Appl. No.: 281,776

[22] Filed: Jul. 9, 1981

[30] Foreign Application Priority Data

Jul. 16, 1980 [JP] Japan .................................. 55-98088
Jul. 18, 1980 [JP] Japan .................................. 55-98957
Jul. 21, 1980 [JP] Japan .................................. 55-100334

[51] Int. Cl.³ .................... C07D 253/06; A01N 43/64
[52] U.S. Cl. ........................................ 71/93; 544/182
[58] Field of Search ............................. 71/93; 544/182

[56] References Cited

FOREIGN PATENT DOCUMENTS 2165554 7/1973 Fed. Rep. of Germany ...... 544/182
1040216 5/1953 France .
1577658 6/1969 France .

OTHER PUBLICATIONS

Daunis et al., *Chemical Abstracts*, vol. 77, 61961a (1972), pp. 504–505.
Doleschall et al., *Tetrahedran*, pp. 1735–1740 (1976) vol. 32.
Gut et al., Collect. Czech. Chem. Comm., 26, 986–997 (1961).
Daunis et al., Bull. Soc. Chem. Fr., No. 4, 1511–1520 (1972).

*Primary Examiner*—John M. Ford
*Attorney, Agent, or Firm*—Birch, Stewart, Kolasch & Birch

[57] ABSTRACT

A herbicidal composition which comprises at least one of triazine compounds of the formula:

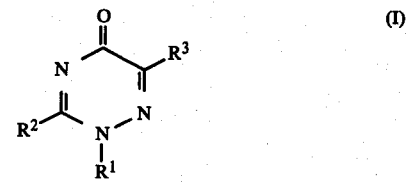

wherein $R^1$ is a $C_1$–$C_4$ alkyl group or an amino group, $R^2$ is a $C_1$–$C_4$ alkoxy group, a $C_1$–$C_4$ alkylthio group or a di($C_1$–$C_4$) alkylamino group and $R^3$ is a cyclo($C_3$–$C_7$) alkyl group, a tertiary $C_4$–$C_5$ alkyl group, an adamantyl group or a group of the formula:

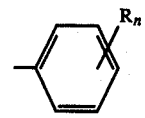

(in which R is a halogen atom, a $C_1$–$C_4$ alkyl group, a $C_1$–$C_4$ alkoxy group, a nitro group or a trihalomethyl group and n is an integer of 0 to 2) in a herbicidally effective amount and an inert carrier or diluent.

15 Claims, No Drawings

5-OXO-2,5-DIHYDRO-1,2,4-TRIAZINES

The present invention relates to 5-oxo-2,5-dihydro-1,2,4-triazines (hereinafter referred to as "triazine compound(s)"), and their production and use.

The triazine compounds are representable by the formula:

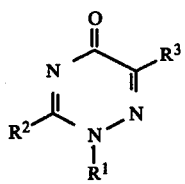

wherein $R^1$ is a $C_1$–$C_6$ alkyl group or an amino group, $R^2$ is a $C_1$–$C_4$ alkoxy group, a $C_1$–$C_4$ alkylthio group or a di($C_1$–$C_4$)alkylamino group and $R^3$ is a cyclo($C_3$–$C_7$)alkyl group, a tertiary $C_4$–$C_5$ alkyl group, an adamantyl group or a group of the formula:

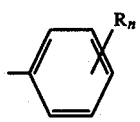

(in which R is a halogen atom, a $C_1$–$C_4$ alkyl group, a $C_1$–$C_4$ alkoxy group, a nitro group or a trihalomethyl group and n is an integer of 0 to 2). In the above significances, the term "halogen" includes chlorine, bromine, fluorine and iodine.

The triazine compounds of the formula (I) have been found to exhibit a prominent herbicidal activity against Gramineae grasses such as barnyard grass (*Echinochloa crus-galli*), large crabgrass (*Digitaria sanguinalis*), green foxtail (*Setaria viridis*), water foxtail (*Alopecurus geniculatus*), annual bluegrass (*Poa annua*), wild oat (*Avena fatua*) and Johnsongrass (*Sorghum halepense*) as well as broad-leaved weeds such as redroot pigweed (*Amaranthus retroflexus*), common lambsquarters (*Chenopodium album*), common purslane (*Portulaca oleracea*), common chickweed (*Stellaria media*), smartweed (*Polygonum scabrum*), catchweed bedstraw (*Galium aparine*), black bindweed (*Polygonum convolvulus*), black nightshade (*Solanum nigrum*), wild mustard (*Sinapis arvensis*), annual morningglory (*Ipomoea purpurea*), jimsonweed (*Datura stramonium*), common ragweed (*Ambrosia artemisifolia*), velvetleaf (*Abutilon theophrasti*), prickly sida (*Sida spinosa*), sicklepod (*Cassia tora*), coffeeweed (*Daubentonia texana*) and cocklebur (*Xanthinum pennsylvanicum*).

Advantageously, the triazine compounds (I) produce a strong herbicidal potency on the application to farmland by soil treatment prior to the germination of grasses and weeds or by foliar treatment at the growth period of grasses and weeds without causing any harmful effect on various crop plants (e.g. corn, wheat, rice plant, cotton, soybean, peanut, sunflower, sugarbeet) and vegetables (e.g. lettuce, tomato). In addition, they may be applied to the paddy field so as to prevent and exterminate the paddy field annual and perennial grasses and weeds such as barnyard grass, pickerel weed (*Monochoria vaginalis*), tooth cup (*Lotala indica*), *Dopatrium junceum*, water starwort (*Callitriche verna*), slender spikerush (*Eleocharis aciculalis*) and hotarui (*Scirpus hotarui*) without causing any phytotoxicity to rice plant.

Accordingly, the triazine compounds (I) are useful as herbicides applicable for paddy field and farmland. They are also useful as herbicides to be employed for orchard, lawn, pasture, tea garden, mulberry field, rubber plantation, forest, non-agricultural land, etc.

Among the triazine compounds, preferred are those of the formula (I) wherein $R^1$ is methyl, $R^2$ is methoxy, methylthio or dimethylamino and $R^3$ is cyclohexyl, t-butyl, adamantyl, phenyl, chlorophenyl, fluorophenyl, trifluoromethylphenyl, methoxyphenyl or methylphenyl. Particularly preferred are those of the formula (I) wherein $R^1$ is methyl, $R^2$ is dimethylamino and $R^3$ is adamanthyl, phenyl or fluorophenyl. When $R^2$ represents a di($C_1$–$C_4$)alkylamino group, the triazine compounds (I) show a particularly strong herbicidal activity on the application to the fields of soybean, wheat, cotton and sugarbeet.

The triazine compounds are novel except 2-methyl-3-methylthio-6-phenyl-5-oxo-2,5-dihydro-1,2,4-triazine (I: $R^1$=—$CH_3$; $R^2$=—$SCH_3$;

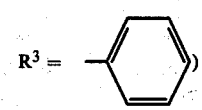

and 2-methyl-3-methoxy-6-phenyl-5-oxo-2,5-dihydro-1,2,4-triazine (I: $R^1$=—$CH_3$; $R^2$=—$OCH_3$;

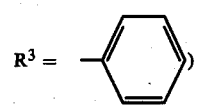

[Bull.Soc.Chim.Fr., 1511 (1972)]. As to these two known compounds, however, any biological activity has never been reported.

The triazine compounds of the formula (I) can be prepared by various procedures, of which typical examples are shown below.

Procedure 1

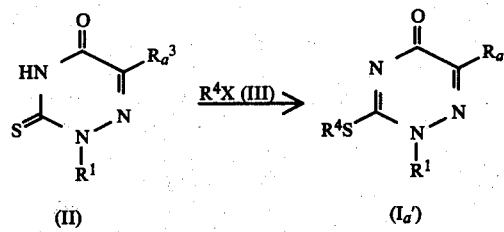

wherein $R^1$ is a $C_1$–$C_6$ alkyl group, $R_a^3$ is a cyclo($C_3$–$C_7$)alkyl group, a tertiary $C_4$–$C_5$ alkyl group, an adamantyl group or a group of the formula:

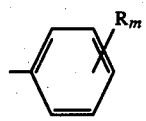

(in which R is as defined above and m is an integer of 1 or 2), $R^4$ is a $C_1$–$C_4$ alkyl group and X is a halogen atom.

The reaction of the thioxo compound (II) with the alkyl halide (III) in the presence of a base affords the alkylthio compound ($I_a'$). The thioxo compound (II) can be synthesized according to the conventional method [Bull.Soc.Chim.Fr., 10, 3658 (1971)]. For example, it may be obtained by reacting an alkyl hydrazine with potassium or ammonium isothiocyanate and reacting the resulting thiosemicarbazide with a substituted or unsubstituted phenyl-α-keto acid. Examples of the alkyl halide (III) are methyl chloride, methyl bromide, methyl iodide, ethyl chloride, ethyl bromide, n-propyl chloride, isopropyl chloride, n-butyl chloride, n-butyl bromide, etc. As the base, there may be employed an alkali metal carbonate (e.g. sodium carbonate, potassium carbonate, lithium carbonate), an alkali metal alkoxide (e.g. sodium methoxide, sodium ethoxide, potassium butoxide), an alkyl alkali metal (e.g. butyl lithium, methyl lithium), an alkali metal hydride (e.g. sodium hydride, potassium hydride), etc.

The molar proportion of the thioxo compound (II) and the alkyl halide (III) in the reaction may be normally from 1:1 to 1:2. The reaction is usually carried out in an inert solvent such as an ether (e.g. tetrahydrofuran), an aromatic hydrocarbon (e.g. benzene, toluene), an alcohol (e.g. methanol), dimethylformamide or water at a temperature of 0° to 100° C., preferably of 25° to 80° C. The reaction is normally accomplished within a period of 1 to 24 hours.

Procedure 2

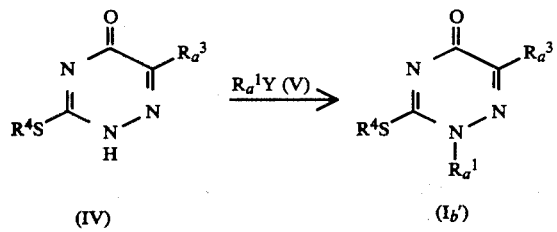

wherein $R_a^1$ is a $C_1$-$C_6$ alkyl group, $R_a^3$ and $R^4$ are each as defined above and Y is a halogen atom.

The reaction of the 2-unsubstituted compound (IV) with the alkyl halide (V) in the presence of a base gives the 2-substituted compound ($I_b'$). The 2-unsubstituted compound (IV) may be synthesized by the conventional method [Bull.Soc.Chim.Fr., 10, 3658 (1971)]. Examples of the alkyl halide (V) are methyl chloride, methyl bromide, methyl iodide, ethyl chloride, ethyl bromide, n-propyl chloride, isopropyl chloride, n-butyl chloride, n-butyl bromide, etc. As the base, there may be employed an alkai metal carbonate (e.g. sodium carbonate, potassium carbonate, lithium carbonate), an alkali metal alkoxide (e.g. sodium methoxide, sodium ethoxide, potassium butoxide), an alkyl alkali metal (e.g. butyl lithium, methyl lithium), an alkali metal hydride (e.g. sodium hydride, potassium hydride), etc.

The molar proportion of the 2-unsubstituted compound (IV) and the alkyl halide (V) in the reaction may be normally from 1:1 to 1:2. The reaction is usually carried out in an inert solvent such as an ether (e.g. tetrahydrofuran), an aromatic hydrocarbon (e.g. benzene, toluene), an alcohol (e.g. methanol), dimethylformamide or water at a temperature of 0° to 80° C., preferably of 0° to 50° C. The reaction is ordinarily accomplished within a period of 1 to 10 hours.

Procedure 3

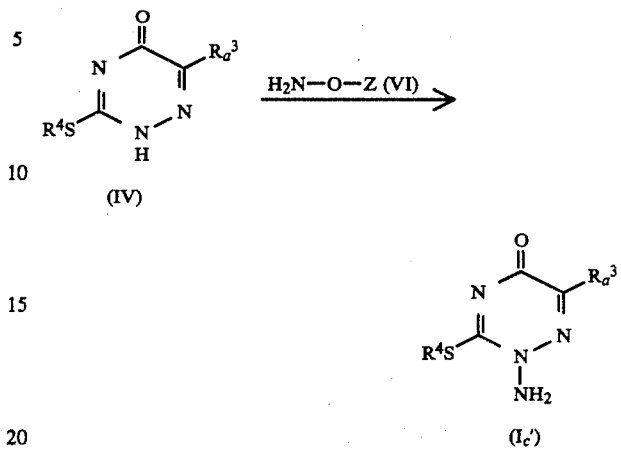

wherein $R_a^3$ and $R^4$ are each as defined above and Z is an acyl group, a sulfonic acid group, a substituted phenylsulfonyl group or a substituted phenyl group.

The reaction of the 2-unsubstituted compound (IV) with the hydroxylamine derivative (VI) in the presence of a base gives the 2-amino compound ($I_c'$). Examples of the hydroxylamine derivative (VI) are hydroxylamine-O-sulfonic acid, O-acetylhydroxylamine, O-hydroylhydroxylamine, O-benzoylhydroxylamine, O-mesitoylbenzoylhydroxylamine, O-(4-nitrobenzoyl)hydroxylamine, O-(3-chlorobenzoyl)hydroxylamine, O-(2,4-dichlorobenzoyl)hydroxylamine, O-(2-iodobenzoyl)hydroxylamine, O-mesitylenesulfonylhydroxylamine, O-(2,4,6-triisopropylbenzenesulfonyl)hydroxylamine, O-picrylhydroxylamine, O-(2,4-dinitrophenyl)hydroxylamine, O-(4-nitrophenyl)hydroxylamine, etc. As the base, there may be employed an alkali metal alkoxide (e.g. sodium methoxide, sodium ethoxide, potassium butoxide), an alkyl alkali metal (e.g. butyl lithium, methyl lithium), an alkali metal hydride (e.g. sodium hydride, potassium hydride), an alkali metal hydroxide (e.g. sodium hydroxide, potassium hydroxide), etc. The reaction is usually carried out in an inert solvent such as water, an alcohol, an ether or dimethylformamide. Depending upon the kind of the base, an appropriate inert solvent may be chosen. The reaction is ordinarily accomplished at a temperature of 20° to 100° C., preferably of 40° to 60° C., within a period of 1 to 10 hours.

Procedure 4

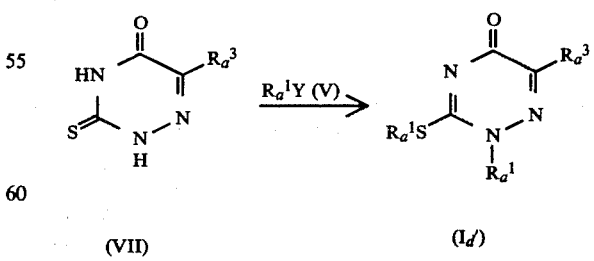

wherein $R_a^1$, $R_a^3$ and Y are each as defined above.

The reaction of the 2-unsubstituted thioxo compound (VII) with the alkyl halide (V) in the presence of a base affords the 2-substituted alkylthio compound ($I_d'$). The 2-unsubstituted thioxo compound (VII) can be readily prepared by condensation of thiosemicarbazide with a substituted or unsubstituted benzoylformic acid according to the conventional method [Angew.Chem., 66, 359 (1964)]. Examples of the alkyl halide (V) are methyl chloride, methyl bromide, methyl iodide, ethyl chloride, ethyl bromide, n-propyl chloride, isopropyl chloride, n-butyl chloride, n-butyl bromide, etc. As the base, there may be employed an alkali metal carbonate (e.g. sodium carbonate, potassium carbonate, lithium carbonate), an alkali metal alkoxide (e.g. sodium methoxide, sodium ethoxide, potassium butoxide), an alkyl alkali metal (e.g. butyl lithium, methyl lithium), an alkali metal hydride (e.g. sodium hydride, potassium hydride), etc.

The molar proportion of the 2-unsubstituted thioxo compound (VII) and the alkyl halide (V) in the reaction may be normally from 1:2 to 1:4. The reaction is usually carried out in an inert solvent such as an ether (e.g. tetrahydrofuran), an aromatic hydrocarbon (e.g. benzene, toluene), an alcohol (e.g. methanol), dimethylformamide or water at a temperature of 0° to 80° C., preferably of 20° to 60° C. The reaction is normally accomplished within a period of 2 to 24 hours.

they may be obtained by reacting the corresponding alkylthio compound (IV) with the dialkylamine (VIII). Examples of the alkyl halide (V) are methyl chloride, methyl bromide, methyl iodide, ethyl chloride, ethyl bromide, n-propyl chloride, isopropyl chloride, n-butyl chloride, n-butyl bromide, etc. As the base, there may be employed an alkai metal carbonate (e.g. sodium carbonate, potassium carbonate, lithium carbonate), an alkali metal alkoxide (e.g. sodium methoxide, sodium ethoxide, potassium butoxide), an alkyl alkali metal (e.g. butyl lithium, methyl lithium), an alkali metal hydride (e.g. sodium hydride, potassium hydride), etc.

The molar proportion of the 2-unsubstituted compound (IX) and the alkyl halide (V) in the reaction may be normally from 1:1 to 1:2. The reaction is usually carried out in an inert solvent such as an ether (e.g. tetrahydrofuran), an aromatic hydrocarbon (e.g. benzene, toluene), an alcohol (e.g. methanol), dimethylformamide or water at a temperature of 0° to 80° C., preferably of 0° to 50° C. The reaction is ordinarily accomplished within a period of 1 to 10 hours.

Procedure 5

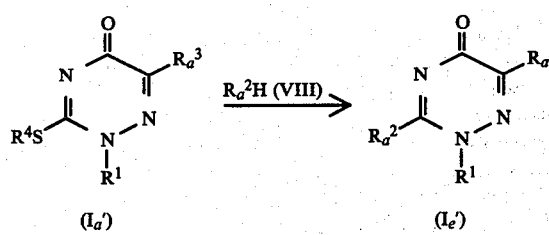

($I_a'$) ($I_e'$)

Procedure 7

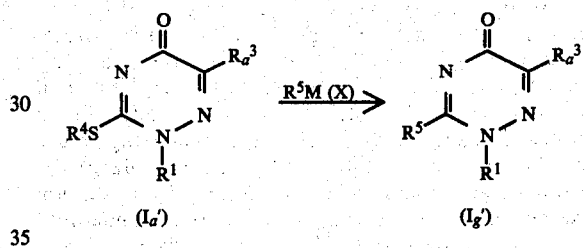

($I_a'$) ($I_g'$)

wherein $R^1$ is as defined above, $R_a^2$ is a di($C_1$-$C_4$)alkylamino group and $R_a^3$ and $R^4$ are each as defined above.

The reaction of the alkylthio compound ($I_a'$) with the dialkylamine (VIII) gives the dialkylamino compound ($I_e'$). Examples of the dialkylamine (VIII) are dimethylamine, methylethylamine, diethylamine, dipropylamine, methylpropylamine, dibutylamine, etc.

The reaction is usually carried out in a polar solvent such as water, acetonitrile, pyridine or dimethylformamide at a temperature of 0° to 100° C., preferably of 30° to 60° C., for a period of 10 minutes to 24 hours. The reaction can proceed under an atmospheric pressure or an elevated pressure (e.g. 3 to 5 atm).

wherein $R^1$, $R_a^3$ and $R^4$ are each as defined above, $R^5$ is a $C_1$-$C_4$ alkoxy group and M is an alkali metal.

The reaction of the alkylthio compound ($I_a'$) with the alkali metal alkoxide (X) produces the alkoxy compound ($I_g'$). As the alkali metal alkoxide (X), there may be used sodium methoxide, sodium ethoxide, potassium butoxide, lithium methoxide, etc.

The reaction is usually carried out in an inert solvent such as an alcohol (e.g. methanol, ethanol), dimethylformamide, an ether (e.g. tetrahydrofuran) or water at a temperature of 20° to 100° C., preferably of 60° to 80° C., for a period of 1 to 10 hours.

The products ($I_a'$) to ($I_g'$) in the above procedures 1 to 7 can be covered by the following single formula:

Procedure 6

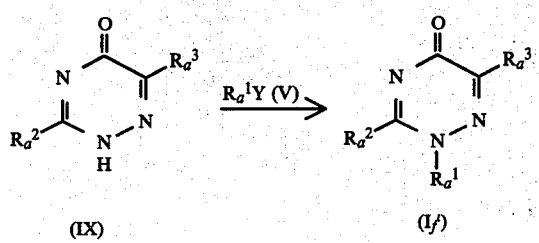

(IX) ($I_f'$)

wherein $R_a^1$, $R_a^2$, $R_a^3$ and Y are each as defined above.

The reaction of the 2-unsubstituted compound (IX) with the alkyl halide (V) in the presence of a base gives the 2-substituted compound ($I_f'$). The 2-unsubstituted compound (IX) can be readily prepared by the known method [J.Prac.Chem., 316, 667 (1974)]. For instance,

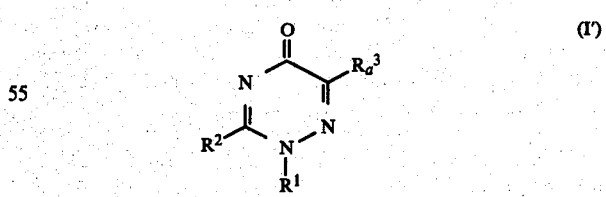

(I')

wherein $R^1$, $R^2$ and $R_a^3$ are each as defined above.

The triazine compounds of the formula (I) which are not covered by the formula (I') can be also produced substantially in the same manner as any of the procedures 1 to 7.

Some practical embodiments of the process for preparing the triazine compounds (I) are illustratively shown below.

EXAMPLE 1

(Procedure 2)

3-Methylthio-6-(o-chlorophenyl)-5-oxo-2,5-dihydro-1,2,4-triazine (0.5 g) was dissolved in tetrahydrofuran (40 ml), and the mixture was cooled to −30° C. with dry ice/acetone. A solution of n-butyl lithium in n-hexane (15%, 1.2 ml) was dropwise added to the mixture, which was then warmed to room temperature. To the resultant mixture, methyl bromide (0.27 g) was dropwise added and, upon completion of the addition, the resulting mixture was stirred at room temperature for 10 hours to complete the reaction. Then, methanol (10 ml) was added thereto, and the resultant mixture was evaporated to dryness under reduced pressure to give a crude product. Recrystallization of the crude product from ethanol gave 0.47 g of 2-methyl-3-methylthio-6-(1-chlorophenyl)-5-oxo-2,5-dihydro-1,2,4-triazine in 90% yield. M.P., 197° C.

Elementary analysis: Calcd. for $C_{11}H_{10}N_3OSCl$: C, 49.35%; H, 3.76%; N, 15.69%. Found: C, 49.21%; H, 3.70%; N, 15.72%.

EXAMPLE 2

(Procedure 6)

3-Dimethylamino-6-(o-methoxyphenyl)-5-oxo-2,5-dihydro-1,2,4-triazine (0.5 g) was dissolved in tetrahydrofuran (40 ml), and the mixture was cooled to −30° C. with dry ice/acetone. A solution of n-butyl lithium in n-hexane (15%, 1.2 ml) was dropwise added to the mixture, which was then warmed to room temperature. To the resultant mixture, methyl iodide (0.42 g) was dropwise added and, upon completion of the addition, the resulting mixture was stirred at room temperature for 10 hours to complete the reaction. Then, methanol (10 ml) was added thereto, and the resultant mixture was evaporated to dryness under reduced pressure to give a crude product. Recrystallization of the crude product from ethanol gave 0.47 g of 2-methyl-3-dimethylamino-6-(o-methoxyphenyl)-5-oxo-2,5-dihydro-1,2,4-triazine in 90% yield. M.P., 202° C.

Elementary analysis: Calcd. for $C_{12}H_{16}N_4O_2$: C, 58.05%; H, 6.50%; N, 22.57%. Found: C, 58.01%; H, 6.43%; N, 22.55%.

EXAMPLE 3

(Procedure 7)

To a solution of 2-methyl-3-methylthio-6-(m-chlorophenyl)-5-oxo-2,5-dihydro-1,2,4-triazine (0.5 g) in methanol (10 ml), sodium methoxide (0.23 g) was added, and the resultant mixture was stirred at room temperature for 2 hours. After stirring, the resulting mixture was evaporated to dryness to give a crude product. Recrystallization of the crude product from ethanol gave 0.28 g of 2-methyl-3-methoxy-6-(m-chlorophenyl)-5-oxo-2,5-dihydro-1,2,4-triazine in 60% yield. M.P., 119° C.

Elementary analysis: Calcd. for $C_{11}H_{10}N_3O_2Cl$: C, 52.5%; H, 4.0%; N, 16.7%. Found: C, 52.3%; H, 4.0%; N, 17.0%.

EXAMPLE 4

(Procedure 7)

2-Methyl-3-methylthio-6-(p-methylphenyl)-5-oxo-2,5-dihydro-1,2,4-triazine (1.0 g) was added in a solution of metallic sodium (0.1 g) in methanol (10 ml), and the resultant mixture was stirred at room temperature for 2 hours. After stirring, the resulting mixture was evaporated to dryness to give a crude product. Recrystallization of the crude product from acetone gave 0.8 g of 2-methyl-3-methoxy-6-(p-methylphenyl)-5-oxo-2,5-dihydro-1,2,4-triazine in 86% yield. M.P., 159° C.

Elementary analysis: Calcd. for $C_{12}H_{13}ON_3$: C, 62.3%; H, 5.6%; N, 18.2%. Found: C, 62.2%; H, 5.7%; N, 18.1%.

EXAMPLE 5

(Procedure 7)

To a solution of 2-methyl-3-methylthio-6-(m-methylphenyl)-5-oxo-2,5-dihydro-1,2,4-triazine (1.0 g) in methanol (10 ml), sodium methoxide (0.5 g) was added, and the resultant mixture was stirred at room temperature for 2 hours. After stirring, the resulting mixture was evaporated to dryness to give a crude product. Recrystallization of the crude product from acetone gave 0.85 g of 2-methyl-3-methoxy-6-(m-methylphenyl)-5-oxo-2,5-dihydro-1,2,4-triazine in 91% yield. M.P., 110° C.

Elementary analysis: Calcd. for $C_{12}H_3ON_3$: C, 52.5%; H, 4.0%; N, 16.7%. Found: C, 52.3%; H, 4.0%; N, 16.8%.

EXAMPLE 6

(Procedure 3)

To a solution of 3-methylthio-6-(p-fluorophenyl)-5-oxo-2,5-dihydro-1,2,4-triazine (2.5 g) in anhydrous dimethylformamide (50 ml), sodium hydride (50% dispersion, 0.5 g) was gradually added and stirred until the generation of hydrogen gas was not detected. o-Mesitylenesulfonylhydroxylamine (2.1 g) was added to the mixture, followed by stirring at room temperature for 6 hours. After completion of the reaction, the resultant mixture was poured into ice-water. The precipitated crystals were collected by filtration. Recrystallization of the obtained crystals from methanol gave 2.0 g of 2-amino-3-methylthio-6-(p-fluorophenyl)-5-oxo-2,5-dihydro-1,2,4-triazine in 74% yield. M.P., 192° C.

Elementary analysis: Calcd. for $C_{10}H_9N_4OSF$: C, 47.61%, H, 3.59%; N, 22.20%. Found: C, 47.53%, H, 3.42%; N, 22.18%.

EXAMPLE 7

(Procedure 5)

2-Amino-3-methylthio-6-(p-chlorophenyl)-5-oxo,-2,5-dihydro-1,2,4-triazine (1.0 g) was added to a mixture of an aqueous solution of 40% dimethylamine (5 ml) and pyridine (10 ml), and the resultant mixture was heated under reflux for 5 hours. After completion of the reaction, the resultant mixture was evaporated to dryness under reduced pressure to give a crude product. Recrystallization of the crude product from acetone gave 0.8 g of 2-amino-3-dimethylamino-6-(p-chlorophenyl)-5-oxo-2,5-dihydro-1,2,4-triazine in 80% yield. M.P., 226° C.

Elementary analysis: Calcd. for $C_{11}H_{12}N_5OCl$: C, 49.72%, H, 4.55%; N, 26.35%. Found: C, 49.59%; H, 4.43%; N, 26.19%.

EXAMPLE 8

(Procedure 5)

2-Amino-3-methylthio-6-(p-fluorophenyl)-5-oxo-2,5-dihydro-1,2,4-triazine (1.0 g) was added to a mixture of an aqueous solution of 40% dimethylamine (5 ml) and acetonitrile (10 ml), and the resultant mixture was heated under reflux for 1 hour. After completion of the reaction, the resultant mixture was evaporated to dryness under reduced pressure to give a crude product. Recrystallization of the crude product from acetone gave 0.7 g of 2-amino-3-dimethylamino-6-(p-fluorophenyl)-5-oxo-2,5-dihydro-1,2,4-triazine in 53% yield. M.P., 212° C.

Elementary analysis: Calcd. for $C_{11}H_{12}N_5OF$: C, 53.01%; H, 4.85%, N, 28.09%. Found: C, 53.15%, H, 4.73%; N, 28.16%.

EXAMPLE 9

(Procedure 3)

3-Methylthio-6-adamantyl-5-oxo-2,5-dihydro-1,2,4-triazine (1.0 g) was dissolved in tetrahydrofuran (20 ml), and the mixture was cooled to −30° C. with dry ice-/acetone. A solution of n-butyl lithium in n-hexane (15%, 3.5 ml) was dropwise added to the mixture, which was then warmed to room temperature. To the resultant mixture, a solution of o-(2,4-dinitrophenyl)hydroxylamine (1.2 g) in tetrahydrofuran (3 ml) was dropwise added and, upon completion of the addition, the resulting mixture was stirred at room temperature for 24 hours to complete the reaction. Then, methanol (20 ml) was added thereto, and the resultant mixture was evaporated to dryness under reduced pressure to give a crude product. The crude product was subjected to purification by silica gel chromatography using a mixture of chloroform and methanol (5:1) as an eluent to give 0.7 g of 2-amino-5-methylthio-6-adamantyl-5-oxo-2,5-dihydro-1,2,4-triazine in 66% yield. M.P., 210° C.

Elementary analysis: Calcd. for $C_{14}H_{20}N_4OS$: C, 57.52%, H, 6.90%; N, 19.17%. Found: C, 57.50%, H, 6.70%; N, 19.08%.

EXAMPLE 10

(Procedure 2)

To a solution of metallic sodium (0.3 g) in dry methanol (20 ml), there were gradually added 3-methylthio-6-cyclohexyl-5-oxo-2,5-dihydro-1,2,4-triazine (2.0 g) and methyl iodide (2.1 g). The resultant mixture was heated at 60° C. for 3 hours while stirring. After completion of the reaction, the resulting solution was made acidic with acetic acid and evaporated to dryness under reduced pressure to give a crude product, followed by purification by silica gel chromatography using a mixture of acetone and n-hexane (1:4) as an eluent to give 1.4 g of 2-methyl-3-thiomethyl-6-cyclohexyl-5-oxo-2,5-dihydro-1,2,4-triazine in 66% yield. M.P., 100°–101° C.

Elementary analysis: Calcd. for $C_{11}H_{17}N_3OS$: C, 55.21%, H, 7.16%, N, 17.56%. Found: C, 55.20%, H, 7.19%; N, 17.60%.

EXAMPLE 11

(Procedure 5)

2-Amino-3-methylthio-6-t-butyl-5-oxo-2,5-dihydro-1,2,4-triazine (1.0 g) was added to a mixture of a 40% aqueous solution of dimethylamine (5 ml) and pyridine (10 ml), and the resulting mixture was heated with reflux for 5 hours. After the reaction was completed, the reaction mixture was evaporated to dryness under reduced pressure to give a crude product. Recrystallization of the crude product from acetone gave 0.8 g of 2-amino-3-dimethylamino-6-t-butyl-5-oxo-2,5-dihydro-1,2,4-triazine in 81% yield. M.P. 168°–169° C.

Elementary analysis: Calcd. for $C_9H_{17}N_5O$: C, 51.16%; H, 8.11%; N, 33.15%. Found: C, 51.15%; N, 8.13%; N, 33.09%.

Some typical examples of the triazine compound (I) are shown in Table 1.

TABLE 1

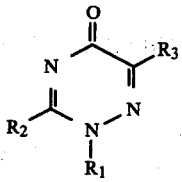

(I)

| Compound No. | $R_1$ | $R_2$ | $R_3$ | Physical constant |
|---|---|---|---|---|
| 1 | $CH_3$ | $(CH_3)_2N-$ | phenyl | M.P. 129° C. |
| 2 | $CH_3$ | $(CH_3)_2N-$ | $CH_3O$-phenyl | M.P. 202° C. |
| 3 | $CH_3$ | $(CH_3)_2N-$ | Br-phenyl | M.P. 164° C. |

TABLE 1-continued (I) Structure: triazinone with R₁ on N, R₂ and R₃ substituents

| Compound No. | R₁ | R₂ | R₃ | Physical constant |
|---|---|---|---|---|
| 4 | CH₃ | (CH₃)₂N— | 3-Cl-C₆H₄— | M.P. 162° C. |
| 5 | CH₃ | (CH₃)₂N— | 3-CF₃-C₆H₄— | M.P. 134° C. |
| 6 | CH₃ | (CH₃)₂N— | 3-CH₃-C₆H₄— | M.P. 101° C. |
| 7 | CH₃ | (CH₃)₂N— | 2-Cl-C₆H₄— | M.P. 168° C. |
| 8 | CH₃ | (CH₃)₂N— | 2-F-C₆H₄— | M.P. 148° C. |
| 9 | CH₃ | (CH₃)₂N— | 2-CH₃-C₆H₄— | M.P. 154° C. |
| 10 | CH₃ | (CH₃)₂N— | 2,4-Cl₂-C₆H₃— | M.P. 225° C. |
| 11 | CH₃CH₂ | (CH₃)₂N— | C₆H₅— | M.P. 131° C. |
| 12 | (CH₃)₂CH | (CH₃)₂N— | C₆H₅— | M.P. 142° C. |
| 13 | CH₃CH₂CH₂ | (CH₃)₂N— | C₆H₅— | M.P. 64° C. |

TABLE 1-continued $$\text{(I)}$$

Structure: 1,2,4-triazin-6(1H)-one with R$_1$ on N1, R$_2$ at 3-position, R$_3$ at 5-position.

| Compound No. | R$_1$ | R$_2$ | R$_3$ | Physical constant |
|---|---|---|---|---|
| 14 | CH$_3$ | (CH$_3$)$_2$N— | 4-NO$_2$-C$_6$H$_4$— | M.P. 165° C. |
| 15 | CH$_3$ | (CH$_3$)$_2$N— | 3,5-Cl$_2$-C$_6$H$_3$— | M.P. 134° C. |
| 16 | CH$_3$ | (CH$_3$)$_2$N— | 2-Cl-4-NO$_2$-C$_6$H$_3$— | M.P. 171° C. |
| 17 | CH$_3$ | (CH$_3$)$_2$N— | 4-F-C$_6$H$_4$— | M.P. 136° C. |
| 18 | CH$_3$ | (CH$_3$)$_2$N— | 4-Cl-C$_6$H$_4$— | M.P. 149° C. |
| 19 | CH$_3$ | (CH$_3$)$_2$N— | 4-CH$_3$-C$_6$H$_4$— | M.P. 137° C. |
| 20 | CH$_3$ | CH$_3$O | 3-Cl-C$_6$H$_4$— | M.P. 119° C. |
| 21 | CH$_3$ | CH$_3$O | 4-CH$_3$-C$_6$H$_4$— | M.P. 159° C. |
| 22 | CH$_3$ | CH$_3$O | 3-CH$_3$-C$_6$H$_4$— | M.P. 110° C. |
| 23 | CH$_3$ | CH$_3$CH$_2$O | C$_6$H$_5$— | M.P. 156° C. |

TABLE 1-continued $$\text{(I)}$$

Structure: 1,2,4-triazin-5(2H)-one with R₃ at position 6, R₂ at position 3, R₁ on N2.

| Compound No. | R₁ | R₂ | R₃ | Physical constant |
|---|---|---|---|---|
| 24 | CH₃ | (CH₃)₂CHO | phenyl | M.P. 105° C. |
| 25 | CH₃CH₂ | CH₃O | phenyl | M.P. 113° C. |
| 26 | (CH₃)₂CH | CH₃O | phenyl | M.P. 109° C. |
| 27 | CH₃ | CH₃O | 2-Cl-phenyl | M.P. 143° C. |
| 28 | CH₃ | CH₃O | 3-CF₃-phenyl | M.P. 109° C. |
| 29 | CH₃CH₂ | CH₃S | phenyl | M.P. 145° C. |
| 30 | CH₃ | CH₃S | 2-Cl-phenyl | M.P. 197° C. |
| 31 | CH₃CH₂ | CH₃CH₂S | phenyl | M.P. 108° C. |
| 32 | CH₃CH₂CH₂ | CH₃S | phenyl | M.P. 129° C. |
| 33 | CH₃ | CH₃CH₂S | phenyl | M.P. 139° C. |
| 34 | CH₃ | CH₃S | 3-CF₃-phenyl | M.P. 127° C. |

TABLE 1-continued
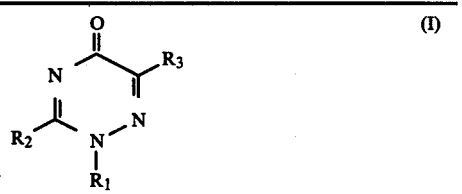
| Compound No. | $R_1$ | $R_2$ | $R_3$ | Physical constant |
|---|---|---|---|---|
| 35 | $CH_3$ | $CH_3S$ | 3-Cl-phenyl | M.P. 158° C. |
| 36 | $CH_3$ | $CH_3S$ | 3-$CH_3$-phenyl | M.P. 162° C. |
| 37 | $CH_3$ | $CH_3S$ | 4-$CH_3$-phenyl | M.P. 152° C. |
| 38 | $CH_3$ | $CH_3S$ | 3-Br-phenyl | M.P. 250° C. |
| 39 | $CH_3$ | $CH_3S$ | 2,4-$Cl_2$-phenyl | M.P. 187° C. |
| 40 | $CH_3$ | $CH_3S$ | 2-$CH_3O$-phenyl | M.P. 192° C. |
| 41 | $(CH_3)_2CH$ | $(CH_3)_2CHS$ | phenyl | M.P. 118–119° C. |
| 42 | $CH_3$ | $CH_3S$ | 4-Cl-phenyl | M.P. 147° C. |
| 43 | $CH_3(CH_2)_4CH_2$ | $CH_3S$ | phenyl | M.P. 68° C. |
| 44 | $(CH_3)_2CH$ | $CH_3S$ | phenyl | M.P. 158° C. |

TABLE 1-continued
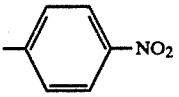
| Compound No. | R₁ | R₂ | R₃ | Physical constant |
|---|---|---|---|---|
| 45 | CH₃ | CH₃S | 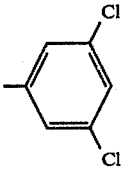 | M.P. 167° C. |
| 46 | CH₃ | CH₃S | 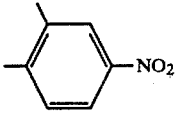 | M.P. 184–185° C. |
| 47 | CH₃ | CH₃S | 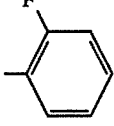 | M.P. 182–185° C. |
| 48 | CH₃ | CH₃S | 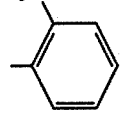 | M.P. 141° C. |
| 49 | CH₃ | CH₃S | 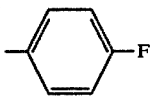 | M.P. 137–139° C. |
| 50 | CH₃ | CH₃S | 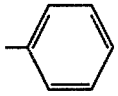 | M.P. 191–193° C. |
| 51 (known) | CH₃ | CH₃S | 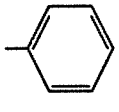 | M.P. 150–151° C. |
| 52 (known) | CH₃ | CH₃O | 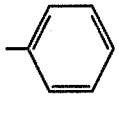 | M.P. 148–149° C. |
| 53 | NH₂ | CH₃S |  | M.P. 224–225° C. |
| 54 | NH₂ | CH₃S | | M.P. 192° C. |

TABLE 1-continued (I)

$$\text{structure with } R_1, R_2, R_3$$

| Compound No. | R₁ | R₂ | R₃ | Physical constant |
|---|---|---|---|---|
| 55 | NH₂ | (CH₃)₂N— | 4-Cl-C₆H₄ | M.P. 226° C. |
| 56 | NH₂ | (CH₃)₂N— | 4-F-C₆H₄ | M.P. 212° C. |
| 57 | NH₂ | CH₃S | 3-CF₃-C₆H₄ | M.P. 204° C. |
| 58 | NH₂ | CH₃S | 3-Br-C₆H₄ | M.P. 190° C. |
| 59 | NH₂ | CH₃S | 4-NO₂-C₆H₄ | M.P. 235° C. |
| 60 | NH₂ | CH₃S | 3-CH₃-C₆H₄ | M.P. 205° C. |
| 61 | NH₂ | (CH₃)₂N— | 2-F-C₆H₄ | M.P. 212° C. |
| 62 | NH₂ | (CH₃)₂N— | 2-CH₃O-C₆H₄ | M.P. 209° C. |
| 63 | NH₂ | (CH₃)₂N— | 3-CF₃-C₆H₄ | M.P. 204° C. |
| 64 | NH₂ | (CH₃)₂N— | 4-CH₃-C₆H₄ | M.P. 177° C. |

TABLE 1-continued $$\text{(I)}$$

Structure: 1,2,4-triazin-6(1H)-one with R$_1$ on N1, R$_2$ on C3, R$_3$ on C5, and =O on C6.

| Compound No. | R$_1$ | R$_2$ | R$_3$ | Physical constant |
|---|---|---|---|---|
| 65 | NH$_2$ | (CH$_3$)$_2$N— | 2-chlorophenyl | M.P. 222° C. |
| 66 | NH$_2$ | (CH$_3$)$_2$N— | 3-chlorophenyl | M.P. 230° C. |
| 67 | NH$_2$ | (CH$_3$)$_2$N— | 4-methylphenyl | M.P. 223° C. |
| 68 | NH$_2$ | CH$_3$S | 4-chlorophenyl | M.P. 216° C. |
| 69 | NH$_2$ | (CH$_3$)$_2$N— | phenyl | M.P. 247° C. |
| 70 | NH$_2$ | CH$_3$S | 1-adamantyl | M.P. 210° C. |
| 71 | —CH$_3$ | CH$_3$S | cyclohexyl | M.P. 100—101° C. |
| 72 | NH$_2$ | (CH$_3$)$_2$N— | (CH$_3$)$_3$C— | M.P. 168–169° C. |
| 73 | NH$_2$ | CH$_3$S | (CH$_3$)$_3$C— | M.P. 160–161° C. |
| 74 | NH$_2$ | CH$_3$S | cyclohexyl | M.P. 180–182° C. |
| 75 | NH$_2$ | CH$_3$O | cyclohexyl | M.P. 117–119° C. |
| 76 | NH$_2$ | (CH$_3$)$_2$N— | cyclohexyl | M.P. 157–158° C. |

TABLE 1-continued $$\text{(I)}$$

[Structure: triazine ring with C=O, R3 at one position, R2 and R1 substituents as shown]

| Compound No. | R₁ | R₂ | R₃ | Physical constant |
|---|---|---|---|---|
| 77 | CH₃ | CH₃S | (CH₃)₂C-CH-C(CH₃)₂ (bicyclic) | $n_D^{20}$ 1.5680 |
| 78 | CH₃ | (CH₃)₂N— | (CH₃)₂C-CH-C(CH₃)₂ (bicyclic) | $n_D^{20}$ 1.5793 |
| 79 | CH₃ | CH₃S | cycloheptyl | $n_D^{20}$ 1.5349 |
| 80 | CH₃ | (CH₃)₂N— | cycloheptyl | $n_D^{20}$ 1.5648 |
| 81 | CH₃ | CH₃S | cyclobutyl | M.P. 103–104° C. |
| 82 | CH₃ | (CH₃)₂N— | cyclobutyl | M.P. 113–114° C. |
| 83 | CH₃ | CH₃S | cyclopentyl | M.P. 72–73° C. |
| 84 | CH₃ | (CH₃)₂N— | cyclohexyl | M.P. 67–80° C. |
| 85 | CH₃ | CH₃S | 1-methylcyclohexyl | M.P. 82–83° C. |
| 86 | CH₃ | (CH₃)₂N— | 1-methylcyclohexyl | $n_D^{20}$ 1.5630 |

TABLE 1-continued

| Compound No. | R₁ | R₂ | R₃ | Physical constant |
|---|---|---|---|---|
| 87 | NH₂ | (CH₃)₂N— |  | M.P. 222–224° C. |
| 88 | CH₃ | (CH₃)₂N— | (CH₃)₃C— | M.P. 93–94° C. |
| 89 | CH₃ | (CH₃)₂N— |  | M.P. 96–98° C. |
| 90 | CH₃ | CH₃S |  | M.P. 186.3° C. |
| 91 | CH₃ | (CH₃)₂N— |  | M.P. 173–174° C. |

In the practical usage of the traizine compounds (I) as herbicides, they may be applied as such or in any preparation form such as wettable powders, emulsifiable concentrate, granules, fine granules, dusts or flowable preparations.

For production of said preparation forms, solid or liquid carriers or diluents may be used. As for the solid carrier or diluent, there may be given mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be given alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent usable for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the triazine compound (I) may be usually from 1 to 80% by weight, preferably from 3 to 50% by weight.

The triazine compound (I) may be used together with other herbicides to improve or enhance its herbicidal activity, and in some cases, to produce a synergistic effect. As the herbicides to be mixed with, there may be given phonoxy series herbicides such as 2,4-dichlorophenoxyacetic acid, 2-methyl-4-chlorophenoxybutyric acid and 2-methyl-4-chlorophenoxyacetic acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; urea series herbicides such as 3-(3,4-dichlorophenyl)-1,1-dimethylurea, 3-(3,4-dichlorophenyl)-1-methoxy-1-methylurea and 1-(2,2-dimethylbenzyl)-3-p-tolylurea; carbamate series herbicides such as isopropyl-N-(3-chlorophenyl)carbamate and methyl-N-(3,4-dichlorophenyl)carbamate; thiolcarbamate series herbicides such as S-(4-chlorobenzyl)-N,N-diethylthiolcarbamate and S-ethyl-N,N-hexamethylenethiolcarbamate; acid anilide series herbicides such as 3,4-dichloropriopionanilide, N-methoxymethyl-2,6-diethyl-α-chloroacetanilide, 2-chloro-2',6'-diethyl-N-butoxymethylacetanilide, 2-chloro-2',6'-diethyl-N-(n-propoxyethyl)acetanilide and N-chloroacetyl-N-(2,6-diethylphenyl)glycine ethyl ester; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4-bispyridinium chloride; phosphorus series herbicides such as N,N-bis(phosphonomethyl)glycine, O-ethyl-O-(2-nitro-5-methylphenyl)-N-sec-butylphosphoroamidothioate, S-(2-methyl-1-piperidylcarbonylmethyl) O-di-n-propyldithiophosphate and S-(2-methyl-1-piperidylcarbonylmethyl) O-diphenyldithiophosphate; toluidine series herbicides such as α,α,α-trifluoro-2,6-dinitro-N,N-dipropyl-p-toluidine; 5-tert-butyl-3-(2,4-dichloro-5-isopropoxyphenyl)-1,3,4-oxadiazolin-2-one; 3-isopropyl-1H-2,1,3-benzothiadiazin(4)-3H-one-2,2-dioxide; α-(β-naphthoxy)propionanilide; 4-(2,4-dichlorobenzoyl)-1,3-dimethylpyrazol-5-yl-p-toluenesulfonate and the like. But, the herbicides are not limited to these examples.

The herbicide of the invention may be applied together with insecticides, nematocides, fungicides, plant growth regulators, fertilizers, etc.

When the triazine compound (I) is used as a herbicide, it may be applied before or after germination of grasses or weeds in an amount within a wide range depending upon its preparation forms, the applied plants or weeds, the soil conditions, etc. Usually, the amount may be usually from about 2–200 grams per are, preferably from about 5–50 grams per are as an active ingredient.

Practical embodiments of the herbicidal composition according to the invention are illustratively shown in the following examples wherein part(s) and % are by weight.

PREPARATION EXAMPLE 1

Twenty-five parts of Compound No. 1, 2.5 parts of a dodecylbenzenesulfonate, 2.5 parts of a ligninsulfonate and 70 parts of diatomaceous earth are well mixed while being powdered to obtain a wettable powder.

PREPARATION EXAMPLE 2

Thirty parts of Compound No. 2, 10 parts of an emulsifier ("Sorpol SM-100" manufactured by Toho Chemical Co., Ltd.) and 60 parts of xylene are well mixed to obtain an emulsifiable concentrate.

PREPARATION EXAMPLE 3

Five parts of Compound No. 3, 1 part of white carbon, 5 parts of a ligninsulfonate and 89 parts of clay are well mixed while being powdered. The mixture is then kneaded with water, granulated and dried to obtain a granule.

PREPARATION EXAMPLE 4

Three parts of Compound No. 5, 1 part of isopropyl phosphate, 66 parts of clay and 30 parts of talc are well mixed while being powdered to obtain a dust.

PREPARATION EXAMPLE 5

Fourty parts of bentonite, 5 parts of a ligninsulfonate and 55 parts of clay are well mixed while being powdered. The mixture is then well kneaded with water, granulated and dried to obtain a granule containing no active ingredient. Ninety-five parts of the thus obtained granule are then impregnated with 5 parts of Compound No. 7 dissolved in methanol. Subsequent removal of methanol gives a granule.

PREPARATION EXAMPLE 6

Ninety-five parts of bentonite of 16-48 mesh is impregnated with 5 parts of Compound No. 8 dissolved in methanol. Subsequent removal of methanol gives a granule.

PREPARATION EXAMPLE 7

Twenty-five parts of Compound No. 53, 2.5 parts of a dodecylbenzenesulfonate, 2.5 parts of a ligninsulfonate and 70 parts of diatomaceous earth are well mixed while being powdered to obtain a wettable powder.

PREPARATION EXAMPLE 8

Thirty parts of Compound No. 54, 10 parts of an emulsifier ("Sorpol SM-100" manufactured by Toho Chemical Co., Ltd.) and 60 parts of xylene are well mixed to obtain an emulsifiable concentrate.

PREPARATION EXAMPLE 9

Five parts of Compound No. 56, 1 part of white carbon, 5 parts of a ligninsulfonate and 89 parts of clay are well mixed while being powdered. The mixture is then kneaded with water, granulated and dried to obtain a granule.

PREPARATION EXAMPLE 10

Three parts of Compound No. 57, 1 part of isopropyl phosphate, 66 parts of clay and 30 parts of talc are well mixed while being powdered to obtain a dust.

PREPARATION EXAMPLE 11

Fourty parts of bentonite, 5 parts of a ligninsulfonate and 55 parts of clay are well mixed while being powdered. The mixture is then well kneaded with water, granulated and dried to obtain a granule containing no active ingredient. Ninety-five parts of the thus obtained granule are then impregnated with 5 parts of Compound No. 59 dissolved in methanol. Subsequent removal of methanol gives a granule.

PREPARATION EXAMPLE 12

Ninety-five parts of bentonite of 16-48 mesh is impregnated with 5 parts of Compound No. 60 dissolved in methanol. Subsequent removal of methanol gives a granule.

Some test examples which show the herbicidal activity of the triazine compound (I) are illustratively shown in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 5, are generally regarded as satisfactory to protect cultivated plants and to control weeds, respectively.

| Rating value | Fresh weight (percentage to untreated plot) | |
|---|---|---|
| | Cultivated plant | Weed |
| 5 | 0-39 | 0 |
| 4 | 40-59 | 1-10 |
| 3 | 60-79 | 11-20 |
| 2 | 80-89 | 21-40 |
| 1 | 90-99 | 41-60 |
| 0 | 100 | 61-100 |

TEST EXAMPLE 1

Pre-emergence soil treatment

Plastic pots (H 10 cm × D 10 cm) were filled with upland field soil, and the seeds of barnyard grass, wild oat, annual morningglory and velvetleaf were separately sowed in the pots. The designed amount of the test compound, each formulated into an emulsifiable concentrate and diluted with water, was sprayed to the soil surface by means of a small hand sprayer, and the treated soil was well mixed to the depth of 3 cm. After the spraying, the test plants were grown in a greenhouse. Twenty days after the treatment, the herbicidal activity was examined. The results are shown in Table 2.

TABLE 2

| Compound No. | Dosage (weight of active ingredient, g/are) | Herbicidal activity | | | |
|---|---|---|---|---|---|
| | | Barnyard grass | Wild oat | Annual morningglory | Velvet-leaf |
| 1 | 40 | 5 | 5 | 5 | 5 |
| | 20 | 5 | 5 | 5 | 5 |
| 2 | 40 | 5 | 5 | 5 | 5 |
| | 20 | 5 | 5 | 5 | 5 |
| 3 | 80 | 5 | 5 | 5 | 5 |
| | 40 | 5 | 5 | 5 | 5 |
| 4 | 80 | 5 | 5 | 5 | 5 |
| | 40 | 5 | 5 | 5 | 5 |
| 5 | 80 | 5 | 5 | 5 | 5 |
| | 40 | 5 | 5 | 5 | 5 |
| 6 | 40 | 5 | 5 | 5 | 5 |
| | 20 | 5 | 5 | 5 | 5 |
| 7 | 80 | 5 | 5 | 5 | 5 |
| | 40 | 5 | 5 | 5 | 5 |
| 8 | 40 | 5 | 5 | 5 | 5 |
| | 20 | 5 | 5 | 5 | 5 |
| 9 | 40 | 5 | 5 | 5 | 5 |
| | 20 | 5 | 5 | 5 | 5 |
| 10 | 40 | 5 | 5 | 5 | 5 |
| | 20 | 5 | 5 | 5 | 5 |
| 11 | 80 | 5 | 5 | 5 | 5 |
| | 40 | 5 | 5 | 5 | 5 |
| 12 | 80 | 5 | 5 | 5 | 5 |
| | 40 | 5 | 5 | 5 | 5 |
| 13 | 80 | 5 | 5 | 5 | 5 |
| | 40 | 5 | 5 | 5 | 5 |
| 14 | 80 | 5 | 5 | 5 | 5 |
| 15 | 80 | 5 | 5 | 5 | 5 |
| 16 | 80 | 5 | 5 | 5 | 5 |
| 17 | 40 | 5 | 5 | 5 | 5 |
| | 20 | 5 | 5 | 5 | 5 |
| 18 | 40 | 5 | 5 | 5 | 5 |
| | 20 | 5 | 5 | 5 | 5 |
| 19 | 40 | 5 | 5 | 5 | 5 |
| | 20 | 5 | 5 | 5 | 5 |
| 71 | 160 | 5 | — | 5 | 5 |
| | 80 | 5 | — | 5 | 5 |
| 73 | 80 | 5 | 5 | 5 | 5 |
| | 40 | — | — | 5 | 5 |
| 74 | 40 | 4 | 4 | 5 | 5 |
| | 20 | — | — | 5 | 5 |
| 75 | 80 | 5 | 5 | 5 | 5 |
| | 40 | 5 | 4 | 5 | 5 |
| 76 | 80 | 5 | — | 5 | 5 |
| | 40 | — | — | 5 | 5 |
| 78 | 80 | 5 | — | 5 | 5 |
| | 40 | 4 | — | 5 | 5 |
| 79 | 160 | 5 | — | 5 | 5 |
| | 80 | — | — | 5 | 5 |
| 80 | 40 | 5 | 5 | 5 | 5 |
| | 20 | 5 | 5 | 5 | 5 |
| 81 | 160 | 5 | 5 | 5 | 5 |
| | 80 | 4 | 4 | 5 | 5 |
| 82 | 80 | 5 | 5 | 5 | 5 |
| | 40 | 5 | 4 | 5 | 5 |
| 83 | 80 | 5 | — | 5 | 5 |
| | 40 | 4 | — | 5 | 5 |
| 84 | 40 | 5 | 5 | 5 | 5 |
| | 20 | 5 | 5 | 5 | 5 |
| 86 | 40 | 5 | 5 | 5 | 5 |
| | 20 | 5 | 4 | 5 | 5 |
| 87 | 40 | 5 | 5 | 5 | 5 |
| | 20 | 5 | 5 | 5 | 5 |
| 89 | 40 | 5 | 5 | 5 | 5 |
| | 20 | 5 | 5 | 5 | 5 |

TEST EXAMPLE 2

Pre-emergence soil treatment

Plastic pots (H 10 cm × D 10 cm) were filled with upland field soil, and the seeds of large crabgrass, redroot pigweed, common purslane and common lambsquarters as well as the seeds of corn were separately sowed in the pots. The designed amount of the test compound, each formulated into an emulsifiable concentrate and diluted with water, was sprayed to the soil surface by means of a small hand sprayer, and the treated soil was well mixed to the depth of 3 cm. After the spraying, the test plants were grown in a greenhouse. Twenty days after the treatment, the herbicidal activity was examined. The results are shown in Table 3.

TABLE 3

| Compound No. | Dosage (weight of active ingredient, g/are) | Herbicidal activity | | | | Phytotoxicity Corn |
|---|---|---|---|---|---|---|
| | | Large crabgrass | Redroot pigweed | Common purslane | Common lambsquarters | |
| 20 | 160 | 5 | 5 | 5 | 5 | 0 |
| | 80 | 5 | 5 | 5 | 5 | 0 |
| 21 | 80 | 5 | 5 | 5 | 5 | 0 |
| | 40 | 5 | 5 | 5 | 5 | 0 |
| 22 | 80 | 5 | 5 | 5 | 5 | 0 |
| | 40 | 5 | 5 | 5 | 5 | 0 |
| 23 | 160 | 5 | 5 | 5 | 5 | 0 |
| | 80 | 4 | 5 | 5 | 5 | 0 |
| 24 | 160 | 4 | 5 | 5 | 5 | 0 |
| | 80 | 4 | 5 | 5 | 5 | 0 |
| 25 | 160 | 5 | 5 | 5 | 5 | 0 |
| | 40 | 4 | 5 | 5 | 5 | 0 |
| 26 | 160 | 3 | 5 | 5 | 4 | 0 |
| 27 | 160 | 4 | 5 | 5 | 5 | 0 |
| | 80 | 4 | 5 | 5 | 5 | 0 |
| 28 | 160 | 4 | 5 | 5 | 5 | 0 |

TABLE 3-continued

| Compound No. | Dosage (weight of active ingredient, g/are) | Herbicidal activity | | | | Phytotoxicity Corn |
|---|---|---|---|---|---|---|
| | | Large crabgrass | Redroot pigweed | Common purslane | Common lambsquarters | |
| | 80 | 3 | 5 | 5 | 5 | 0 |
| 29 | 160 | 4 | 5 | 4 | 5 | 0 |
| | 80 | 3 | 4 | 4 | 5 | 0 |
| 30 | 160 | 5 | 5 | 5 | 5 | 0 |
| | 80 | 5 | 5 | 5 | 5 | 0 |
| 31 | 160 | 3 | 5 | 4 | 5 | 0 |
| 32 | 160 | 3 | 5 | 5 | 5 | 0 |
| 33 | 160 | 5 | 5 | 5 | 5 | 0 |
| | 80 | 4 | 5 | 5 | 5 | 0 |
| 34 | 160 | 3 | 5 | 5 | 5 | 0 |
| 35 | 160 | 5 | 5 | 5 | 5 | 0 |
| | 80 | 4 | 5 | 5 | 5 | 0 |
| 36 | 160 | 4 | 5 | 5 | 5 | 0 |
| | 80 | 4 | 4 | 4 | 5 | 0 |
| 37 | 160 | 5 | 5 | 5 | 5 | 0 |
| | 80 | 4 | 4 | 5 | 5 | 0 |
| 38 | 160 | 4 | 5 | 4 | 5 | 0 |
| 39 | 160 | 5 | 5 | 5 | 5 | 0 |
| 40 | 160 | 5 | 5 | 5 | 5 | 0 |
| | 80 | 5 | 5 | 5 | 5 | 0 |
| 41 | 160 | 3 | 4 | 4 | 5 | 0 |
| 42 | 160 | 4 | 5 | 5 | 5 | 0 |
| 43 | 160 | 3 | 5 | 4 | 5 | 0 |
| 44 | 160 | 3 | 5 | 5 | 5 | 0 |
| 45 | 160 | 3 | 4 | 4 | 5 | 0 |
| 46 | 160 | 4 | 4 | 4 | 5 | 0 |
| 47 | 160 | 3 | 5 | 5 | 5 | 0 |
| 48 | 160 | 4 | 5 | 5 | 5 | 0 |
| | 80 | 4 | 5 | 5 | 5 | 0 |
| 49 | 160 | 5 | 5 | 5 | 5 | 0 |
| | 80 | 5 | 5 | 5 | 5 | 0 |
| 50 | 160 | 5 | 5 | 5 | 5 | 0 |
| | 80 | 5 | 5 | 5 | 5 | 0 |
| 53 | 160 | 5 | 5 | 5 | 5 | 0 |
| | 80 | 5 | 5 | 5 | 5 | 0 |
| 55 | 160 | 5 | 5 | 5 | 5 | 0 |
| | 80 | 5 | 5 | 5 | 5 | 0 |
| 60 | 160 | 5 | 5 | 5 | 5 | 0 |
| | 80 | 5 | 5 | 5 | 5 | 0 |
| 68 | 160 | 5 | 5 | 5 | 5 | 0 |
| | 80 | 5 | 5 | 5 | 5 | 0 |
| 69 | 160 | 5 | 5 | 5 | 5 | 0 |
| | 80 | 5 | 5 | 5 | 5 | 5 |

TEST EXAMPLE 3

Pre-emergence foliar treatment

Plastic trays (35 cm×25 cm×10 cm) were filled with upland field soil, and the seeds of barnyard grass, wild oat, wild mustard and velvetleaf were separately sowed in the trays and grown for 2 weeks in a greenhouse. The designed amount of the test compound, each formulated into an emulsifiable concentrate, was sprayed to the foliage of the test plants over the top by means of a small hand sprayer. After the spraying, the test plants were grown for further 3 weeks in the greenhouse, and the herbicidal activity was examined. The results are shown in Table 4. In this treatment, the emulsifiable concentrate was dispersed in water containing a wetting agent for application at a spray volume of 5 liters per are.

TABLE 4

| Compound No. | Dosage (weight of active ingredient, g/are) | Herbicidal activity | | | |
|---|---|---|---|---|---|
| | | Barnyard grass | Wild oat | Wild mustard | Velvetleaf |
| 1 | 40 | 5 | 5 | 5 | 5 |
| | 20 | 5 | 5 | 5 | 5 |
| 2 | 40 | 5 | 5 | 5 | 5 |
| | 20 | 4 | 4 | 5 | 5 |
| 3 | 40 | 5 | 5 | 5 | 5 |
| | 20 | 5 | 5 | 5 | 5 |
| 5 | 40 | 5 | 5 | 5 | 5 |
| | 20 | 5 | 5 | 5 | 5 |
| 8 | 40 | 5 | 5 | 5 | 5 |
| | 20 | 5 | 5 | 5 | 5 |
| 9 | 40 | 5 | 5 | 5 | 5 |
| | 20 | 5 | 5 | 5 | 5 |
| 10 | 40 | 5 | 5 | 5 | 5 |
| | 20 | 4 | 5 | 5 | 5 |
| 15 | 40 | 4 | 5 | 5 | 5 |
| | 20 | 3 | 5 | 5 | 5 |
| 17 | 40 | 5 | 5 | 5 | 5 |
| | 20 | 5 | 5 | 5 | 5 |
| 18 | 40 | 5 | 5 | 5 | 5 |
| | 20 | 5 | 5 | 5 | 5 |
| 19 | 40 | 5 | 5 | 5 | 5 |
| | 20 | 5 | 5 | 5 | 5 |
| 20 | 40 | 4 | — | 5 | 5 |
| 21 | 40 | 5 | — | 5 | 5 |
| 22 | 40 | 5 | — | 5 | 5 |
| 25 | 40 | 4 | — | 5 | 5 |
| 51 | 40 | 5 | 5 | 5 | 5 |
| | 20 | 5 | 4 | 4 | 5 |
| 52 | 40 | 5 | 5 | 5 | 5 |
| | 20 | 5 | 4 | 5 | 5 |
| 53 | 40 | 5 | — | 5 | 5 |
| 54 | 40 | 5 | — | 5 | 5 |
| 55 | 40 | 4 | — | 5 | 5 |
| 56 | 40 | 5 | — | 5 | 5 |
| 57 | 40 | 5 | — | 5 | 5 |
| 58 | 40 | 4 | — | 4 | 5 |
| 59 | 40 | 4 | — | 4 | 4 |
| 60 | 40 | 5 | — | 5 | 5 |
| 61 | 40 | 4 | — | 5 | 5 |
| 62 | 40 | 5 | — | 5 | 5 |
| 63 | 40 | 4 | — | 5 | 5 |
| 64 | 40 | 5 | — | 5 | 5 |
| 65 | 40 | 5 | — | 5 | 5 |
| 66 | 40 | 5 | — | 5 | 5 |
| 67 | 40 | 5 | — | 5 | 5 |
| 68 | 40 | 4 | — | 4 | 5 |
| 69 | 40 | 5 | — | 5 | 5 |
| 72 | 40 | 5 | 5 | 5 | 5 |
| 73 | 40 | 5 | 5 | 5 | 5 |
| 74 | 40 | 5 | 5 | 5 | 5 |
| 75 | 40 | 5 | 5 | 5 | 5 |
| 77 | 40 | — | — | 5 | 5 |
| 79 | 20 | — | — | 5 | 5 |
| | 10 | — | — | 5 | 5 |
| 80 | 40 | 5 | 5 | 5 | 5 |
| | 20 | 5 | 5 | 5 | 5 |
| 82 | 40 | 5 | 5 | 5 | 5 |
| 83 | 40 | 5 | 4 | 5 | 5 |
| 84 | 20 | 5 | 5 | 5 | 5 |
| | 10 | 5 | 5 | 5 | 5 |
| 85 | 20 | — | — | 5 | 5 |
| 86 | 20 | 5 | 5 | 5 | 5 |
| | 10 | 5 | 5 | 5 | 5 |
| 87 | 40 | 5 | 5 | 5 | 5 |
| 88 | 40 | 5 | 5 | 5 | 5 |
| 89 | 20 | 5 | 5 | 5 | 5 |
| | 10 | 5 | 5 | 5 | 5 |
| 91 | 20 | 5 | 5 | 5 | 5 |
| | 10 | 5 | 5 | 5 | 5 |

TEST EXAMPLE 4

Pre-emergence soil treatment

Plastic trays (35 cm×25 cm×10 cm) were filled with upland field soil, and the seeds of redroot pigweed, common lambsquarters, annual morningglory, cocklebur, velvetleat, coffeeweed, prickly sida and large crabgrass and the seeds of soybean and corn were separately sowed in the trays. The designed amount of the test compound, each formulated into a wettable powder, was sprayed to the soil surface by means of a small hand sprayer. After the spraying, the test plants were grown in a greenhouse. Twenty days after the treatment, the herbicidal activity and the phytotoxicity were examined. The results are shown in Table 5. In this treatment, the wettable powder was dispersed in water for application at a spray volume of 5 liters per are.

treatment, the wettable powder was dispersed in water for application at a spray volume of 5 liters per are.

TABLE 6

| Compound No. | Dosage (weight of active ingredient, g/are) | Herbicidal Activity | | | | | Phytotoxicity | |
| --- | --- | --- | --- | --- | --- | --- | --- | --- |
| | | Redroot pigweed | Common lambsquarters | Annual morningglory | Velvetleaf | Green foxtail | Cotton | Corn |
| 51 | 80 | 5 | 5 | 5 | 5 | 5 | 0 | 0 |
|  | 40 | 5 | 5 | 5 | 5 | 5 | 0 | 0 |
| 52 | 80 | 5 | 5 | 5 | 5 | 5 | 0 | 0 |
|  | 40 | 5 | 5 | 5 | 5 | 5 | 0 | 0 |

TEST EXAMPLE 6

Post-emergence foliar treatment

Plastic trays (35 cm×25 cm×10 cm) were filled with upland field soil, and the seeds of redroot pigweed, common lambsquarters, velvetleaf, annual morningglory, cocklebur, sunflower and black bindweed and the seeds of corn and wheat were separately sowed in the trays and grown for 3 weeks in a greenhouse. The

TABLE 5

| Compound No. | Dosage (weight of active ingredient, g/are) | Herbicidal activity | | | | | | | | Phytotoxicity | |
| --- | --- | --- | --- | --- | --- | --- | --- | --- | --- | --- | --- |
| | | Redroot pigweed | Common lambsquarters | Annual morningglory | Cocklebur | Velvetleaf | Coffeeweed | Prickly sida | Large crabgrass | Soybean | Corn |
| 1 | 40 | 5 | 5 | 5 | 5 | 5 | 5 | 5 | 5 | 1 | 1 |
|  | 20 | 5 | 5 | 5 | 5 | 5 | 5 | 5 | 5 | 0 | 0 |
| 10 | 40 | 5 | 5 | 5 | 5 | 5 | 5 | 5 | 5 | 0 | 0 |
|  | 20 | 5 | 5 | 4 | 4 | 5 | 5 | 5 | 5 | 0 | 0 |
| 18 | 40 | 5 | 5 | 5 | 5 | 5 | 5 | 5 | 5 | 1 | 1 |
|  | 20 | 5 | 5 | 4 | 4 | 5 | 5 | 5 | 5 | 0 | 0 |
| 19 | 40 | 5 | 5 | 5 | 5 | 5 | 5 | 5 | 5 | 1 | 0 |
|  | 20 | 5 | 5 | 5 | 5 | 4 | 5 | 5 | 5 | 0 | 0 |
| 88 | 10 | 5 | 5 | 5 | 4 | 5 | 5 | 5 | 4 | 1 | 0 |
|  | 5 | 5 | 5 | 5 | 2 | 5 | 3 | 5 | 2 | 0 | 0 |
| 89 | 10 | 5 | 5 | 5 | 5 | 5 | 5 | 5 | 4 | 1 | 0 |
|  | 5 | 5 | 5 | 5 | 3 | 5 | 3 | 5 | 3 | 0 | 0 |
| Control (A)* | 40 | 5 | 5 | 5 | 5 | 5 | 5 | 4 | 5 | 3 | 5 |
|  | 20 | 5 | 5 | 5 | 4 | 3 | 5 | 2 | 5 | 2 | 5 |

Note:
*Diuron

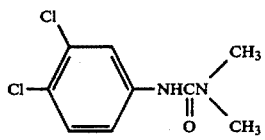

TEST EXAMPLE 5

Pre-emergence soil treatment

Plastic trays (35 cm×25 cm×10 cm) were filled with upland field soil, and the seeds of redroot pigweed, common lambsquarters, annual morningglory, velvetleaf, green foxtail and the seeds of cotton and corn were separately sowed in the trays. The designed amount of the test compound, each formulated into a wettable powder, was sprayed to the soil surface by means of a small hand sprayer. After the spraying, the test plants were grown in a greenhouse. Twenty days after the treatment, the herbicidal activity and the phytotoxicity were examined. The results are shown in Table 6. In this designed amount of the test compound, each formulated into an emulsifiable concentrate, was sprayed to the foliage of the test plants over the top by means of a small hand sprayer. After the spraying, the test plants were grown for further 3 weeks in the greenhouse, and the herbicidal activity and phytotoxicity were examined. The results are shown in Table 7. In this treatment; the emulsifiable concentrate was dispersed in water containing a wetting agent for application at a spray volume of 5 liters per are.

The growing stage of the test plants varied on their kind. However, the weeds were generally at 2 to 4 leaved stage and in 2 to 10 cm heights, and corn and wheat were each at 2 leaved stage.

TABLE 7

| Compound No. | Dosage (weight of active ingredient, g/are) | Herbicidal Activity | | | | | | | Phytotoxicity | |
|---|---|---|---|---|---|---|---|---|---|---|
| | | Redroot pigweed | Common lambs-quarters | Velvetleaf | Annual morningglory | Cocklebur | Sunflower | Black bindgrass | Corn | Wheat |
| 1 | 5 | 5 | 5 | 5 | 5 | 5 | 5 | 5 | 1 | 1 |
|   | 2.5 | 5 | 5 | 5 | 4 | 5 | 5 | 5 | 0 | 0 |
| 18 | 5 | 5 | 5 | 5 | 5 | 5 | 5 | 5 | 1 | 1 |
|   | 2.5 | 4 | 5 | 5 | 5 | 5 | 5 | 5 | 0 | 0 |
| Control (B)* | 5 | 5 | 5 | 4 | 5 | 5 | 5 | 5 | 0 | 4 |
|   | 2.5 | 5 | 5 | 3 | 4 | 4 | 5 | 5 | 0 | 2 |

Note:
*Atrazine

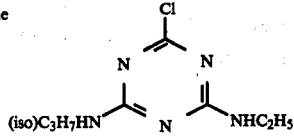

TEST EXAMPLE 7

Post-emergence foliar treatment

Plastic trays (35 cm×25 cm×10 cm) were filled with upland field soil, and the seeds of redroot pigweed, common lambsquarters, prickly sida and annual morningglory and weeds of cotton were separately sowed in the trays and grown for 3 weeks in a greenhouse. The designed amount of the test compound each formulated into an emulsifiable concentrate was sprayed to the foliage of the test plants over the top by means of a small hand sprayer. After the spraying, the test plants were grown for further 3 weeks in the greenhouse, and the herbicidal activity and phytotoxicity were examined. The results are shown in Table 8. In this treatment, the emulsifiable concentrate was dispersed in water containing a wetting agent for application at a spray volume of 5 liters per are.

The growing stage of the test plants varied on their kind. However, the weeds were generally at 2 to 4 leaved stage and in 2 to 10 cm heights, and cotton was at 1 leaved stage and in 10 cm heights.

TABLE 8

| Compound No. | Dosage (weight of active ingredient, g/are) | Herbicidal Activity | | | | Phytotoxicity Cotton |
|---|---|---|---|---|---|---|
| | | Redroot pigweed | Common lambsquarters | Prickly sida | Annual morningglory | |
| 69 | 40 | 5 | 5 | 5 | 5 | 0 |
|   | 20 | 5 | 5 | 5 | 4 | 0 |
| Control (C)* | 10 | 5 | 5 | 3 | 4 | 5 |
|   | 5 | 5 | 5 | 0 | 3 | 2 |

Note:
*DCMU, i.e. 3-(3,4-dichlorophenyl)-1,1-dimethylurea

TEST EXAMPLE 8

Paddy field treatment

Plastic pots (each 500 ml volume) were filled with paddy field soil containing the seeds of various weeds and, water was poured therein until the depth of water became 4 cm. Rice seedlings of 2 leaved stage and buds of slender spikerush, which tided over the winter, were planted into the pots and grown for 5 days in a greenhouse. The designed amount of the test compound each formulated into an emulsifiable concentrate was applied to the pots by perfusion. After the application, the test plants were further grown for 3 weeks in the greenhouse and the herbicidal activity and phytotoxicity were checked on the plants as well as the weeds such as barnyard grass, broad-leaved weeds (e.g. pickerel weed, false pimpernel, toothcup) which were previously sowed in the paddy field soil. The results are shown in Table 9. In this treatment, the emulsifiable concentrate was dispersed in water for application at a perfusion volume of 10 liters per are.

TABLE 9

| Compound No. | Dosage (weight of active ingredient, g/are) | Herbicidal activity | | | Phytotoxicity Rice plant |
|---|---|---|---|---|---|
| | | Barnyard grass | Broad-leaved grass | Slender spikerush | |
| 32 | 80 | 4 | 5 | 5 | 0 |
|   | 40 | 3 | 5 | 3 | 0 |
| 42 | 80 | 4 | 5 | 4 | 0 |
|   | 40 | 4 | 5 | 4 | 0 |
| 44 | 80 | 4 | 5 | 4 | 0 |
|   | 40 | 3 | 4 | 3 | 0 |
| 49 | 80 | 4 | 5 | 4 | 0 |
|   | 40 | 3 | 5 | 4 | 0 |
| 50 | 80 | 5 | 5 | 5 | 0 |
|   | 40 | 4 | 5 | 4 | 0 |
| 70 | 40 | 5 | 5 | 4 | 0 |
| 80 | 40 | 5 | 5 | 5 | 0 |
|   | 20 | 5 | 5 | 4 | 0 |
| 81 | 40 | 5 | 5 | 4 | 0 |
|   | 20 | 5 | 5 | 4 | 0 |
| 84 | 40 | 5 | 5 | 5 | 0 |
|   | 20 | 5 | 5 | 5 | 0 |
| 86 | 40 | 5 | 5 | 4 | 0 |
|   | 20 | 5 | 5 | 4 | 0 |
| 89 | 40 | 5 | 5 | 4 | 0 |
| 90 | 40 | 5 | 5 | — | 0 |
| 91 | 40 | 5 | 5 | 5 | 0 |

What is claimed is:

1. A herbicidal composition suitable for agricultural use which comprises at least one triazine compound of the formula:

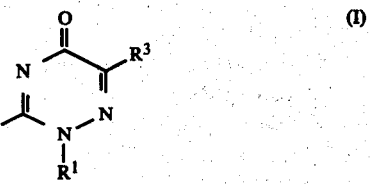

(I)

wherein $R^1$ is a $C_1$-$C_6$ alkyl group or an amino group, $R^2$ is a $C_1$-$C_4$ alkoxy group, a $C_1$-$C_4$ alkylthio group or a di($C_1$-$C_4$) alkylamino group and $R^3$ is a cyclo($C_3$-C-

7)alkyl group, a tertiary C4–C5 alkyl group, an adamantyl group or a group of the formula:

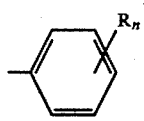

in which R is a halogen atom, a C1–C4 alkyl group, a C1–C4 alkoxy group, a nitro group or a trihalomethyl group and n is an integer of 0 to 2 in a herbicidally effective amount and an inert carrier or diluent.

2. The composition according to claim 1, wherein $R^1$ is methyl, $R^2$ is methoxy, methylthio or dimethylamino and $R^3$ is cyclohexyl, t-butyl, adamantyl, phenyl, chlorophenyl, fluorophenyl, trifluoromethylphenyl, methoxyphenyl or methylphenyl.

3. The composition according to claim 1, wherein $R^1$ is methyl, $R^2$ is dimethylamino and $R^3$ is adamantyl, phenyl or fluorophenyl.

4. The composition according to claim 1, in the form of an emulsifiable concentrate wherein said inert carrier or diluent is a liquid carrier.

5. The composition according to claim 1, in the form of an aqueous emulsion.

6. The composition according to claim 1, in the form of a wettable powder.

7. A triazine compound of the formula:

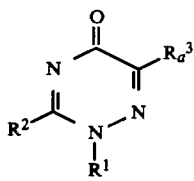

(I')

wherein $R^1$ is a C1–C6 alkyl group or an amino group, $R^2$ is a C1–C4 alkoxy group, a C1–C4 alkylthio group or a di(C1–C4)alkylamino group and $R_a^3$ is a cyclo(C3–C7)alkyl group, a tertiary C4–C5 alkyl group, an adamantyl group or a group of the formula:

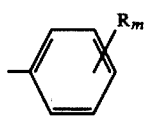

in which R is a halogen atom, a C1–C4 alkyl group, a C1–C4 alkoxy group, a nitro group or a trihalomethyl group and m is an integer of 1 or 2.

8. The compound according to claim 7, wherein $R^2$ is C1–C4 alkylthio.

9. The compound according to claim 7, wherein $R^2$ is C1–C4 alkoxy.

10. A method for exterminating weeds and/or grasses which comprises applying a herbicidally effective amount of at least one triazine compound of the formula:

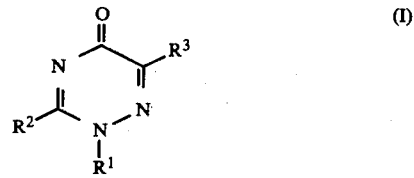

(I)

wherein $R^1$ is a C1–C6 alkyl group or an amino group, $R^2$ is a C1–C4 alkoxy group, a C1–C4 alkylthio group or a di(C1–C4)alkylamino group and $R_3$ is a cyclo(C3–C7)alkyl group, a tertiary C4–C5 alkyl group, an adamantyl group or a group of the formula:

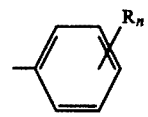

in which R is a halogen atom, a C1–C4 alkyl group, a C1–C4 alkoxy group, a nitro group or a trihalomethyl group and n is an integer of 0 to 2 to the area wherein the weeds and/or grasses grow or will grow.

11. The method according to claim 10, wherein $R^2$ is di(C1–C4)alkylamino.

12. The method according to claim 10, wherein the area where the application is made is a field of soybean, wheat, cotton or sugarbeet.

13. A triazine compound of the formula:

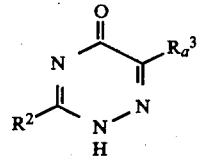

wherein $R^2$ is a C1–C4 alkoxy group, a C1–C4 alkylthio group or a di(C1–C4)alkylamino group and $R_a^3$ is a cyclo(C3–C7)alkyl group, a tertiary C4–C5 alkyl group, an adamantyl group or a group of the formula:

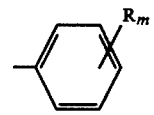

in which R is a halogen atom, a C1–C4 alky group, a C1–C4 alkoxy group, a nitro group or a trihalomethyl group and m is an integer of 1 or 2.

14. A triazine compound of the formula:

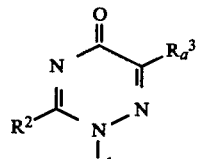

(I')

wherein $R^1$ is a C1–C6 alkyl group or an amino group, $R^2$ is a di(C1–C4)alkylamino group and $R_a^3$ is a cyclo(C3–C7)alkyl group, a tertiary C4–C5 alkyl group, an adamantyl group or a group of the formula

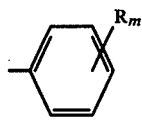

in which R is a halogen atom, a $C_1$–$C_4$ alkyl group, a $C_1$–$C_4$ alkoxy group, a nitro group or a trihalomethyl group and m is an integer of 1 or 2.

15. A triazine compound of the formula:

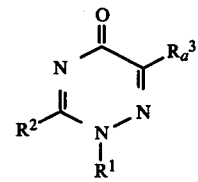

wherein $R^1$ is an amino group, $R^2$ is a $C_1$–$C_4$ alkoxy group, a $C_1$–$C_4$ alkylthio group of a di($C_1$–$C_4$)alkylamino group and $R_a^3$ is a cyclo($C_3$–$C_7$)alkyl group, a tertiary $C_4$–$C_5$ alkyl group, an adamantyl group or a group of the formula

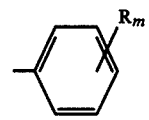

in which R is a halogen atom, a $C_1$–$C_4$ alkyl roup, a $C_1$–$C_4$ alkoxy group, a nitro group or a trihalomethyl group and m is an integer of 1 or 2.

* * * * *